(12) United States Patent
Golini

(10) Patent No.: US 12,029,762 B2
(45) Date of Patent: *Jul. 9, 2024

(54) ALKALIZED ORGANIC PHARMACEUTICAL OR NUTRACEUTICAL COMPOSITION

(71) Applicant: Jeffrey M. Golini, Billings, MT (US)

(72) Inventor: Jeffrey M. Golini, Billings, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/828,573

(22) Filed: May 31, 2022

(65) Prior Publication Data

US 2022/0288126 A1 Sep. 15, 2022

Related U.S. Application Data

(60) Continuation of application No. 17/023,150, filed on Sep. 16, 2020, now Pat. No. 11,376,282, which is a continuation of application No. 15/948,868, filed on Apr. 9, 2018, now abandoned, which is a continuation of application No. 15/096,166, filed on Apr. 11, 2016, now abandoned, which is a division of application No. 13/998,672, filed on Nov. 21, 2013, now abandoned, which is a continuation of application No. 12/807,067, filed on Aug. 26, 2010, now abandoned.

(60) Provisional application No. 61/275,190, filed on Aug. 26, 2009.

(51) Int. Cl.

| | |
|---|---|
| *A61K 35/20* | (2006.01) |
| *A23L 5/00* | (2016.01) |
| *A23L 29/30* | (2016.01) |
| *A23L 33/00* | (2016.01) |
| *A23L 33/105* | (2016.01) |
| *A23L 33/115* | (2016.01) |
| *A23L 33/125* | (2016.01) |
| *A23L 33/15* | (2016.01) |
| *A23L 33/16* | (2016.01) |
| *A23L 33/175* | (2016.01) |
| *A23L 33/185* | (2016.01) |
| *A23L 33/19* | (2016.01) |
| *A61K 31/198* | (2006.01) |
| *A61K 31/337* | (2006.01) |
| *A61K 31/661* | (2006.01) |
| *A61K 31/718* | (2006.01) |
| *A61K 33/00* | (2006.01) |
| *A61K 33/42* | (2006.01) |
| *A61K 36/185* | (2006.01) |
| *A61K 36/889* | (2006.01) |
| *A61K 36/899* | (2006.01) |
| *A61K 36/90* | (2006.01) |
| *A61K 38/16* | (2006.01) |
| *A61K 45/06* | (2006.01) |

(52) U.S. Cl.
CPC ............... *A61K 35/20* (2013.01); *A23L 5/00* (2016.08); *A23L 29/30* (2016.08); *A23L 33/105* (2016.08); *A23L 33/115* (2016.08); *A23L 33/125* (2016.08); *A23L 33/15* (2016.08); *A23L 33/16* (2016.08); *A23L 33/175* (2016.08); *A23L 33/185* (2016.08); *A23L 33/19* (2016.08); *A23L 33/30* (2016.08); *A61K 31/198* (2013.01); *A61K 31/337* (2013.01); *A61K 31/661* (2013.01); *A61K 31/718* (2013.01); *A61K 33/00* (2013.01); *A61K 33/42* (2013.01); *A61K 36/185* (2013.01); *A61K 36/889* (2013.01); *A61K 36/899* (2013.01); *A61K 36/90* (2013.01); *A61K 38/168* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 2,357,069 A | 8/1944 | Barackman |
| 3,392,195 A | 7/1968 | Galat |
| 4,267,197 A | 5/1981 | Sawhill |
| 4,994,284 A | 2/1991 | Miller |
| 5,506,248 A | 4/1996 | Nikfar et al. |
| 5,612,375 A | 3/1997 | Sueoka |
| 5,637,324 A | 6/1997 | Bland |
| 5,973,005 A | 10/1999 | D'Amelio, Sr et al. |
| 6,399,661 B1 | 6/2002 | Golini |
| 6,451,361 B1 | 9/2002 | Moore |

(Continued)

FOREIGN PATENT DOCUMENTS

| | | |
|---|---|---|
| DE | 43 20 853 A1 | 1/1995 |
| EP | 1 520 580 A1 | 4/2005 |

(Continued)

OTHER PUBLICATIONS bodybuildingforyou.com, internet article obtained from the internet archive, published 2008, https://web.archive.org/web/20080222030534/http://www.bodybuildingforyou.com/supplements-reviews/glutamine.htm. (Year: 2008).*

(Continued)

*Primary Examiner* — Layla D Berry
(74) *Attorney, Agent, or Firm* — Seed IP Law Group LLP

(57) ABSTRACT

The invention relates to a pharmaceutical or nutraceutical composition comprising an alkalized organic substance selected from the group comprising proteins, carbohydrates, lipids, amino acids, vitamins, therapeutic agents and mixtures thereof. Such compositions are useful for treating a range of diseases and conditions. They also give rise to beneficial physiological effects such as, for example, increasing physical strength, muscle mass and endurance.

11 Claims, 3 Drawing Sheets

(56) References Cited

U.S. PATENT DOCUMENTS

| | | |
|---|---|---|
| 2002/0055540 A1 | 5/2002 | Golini |
| 2004/0071752 A1 | 4/2004 | Hornack et al. |
| 2007/0142325 A1 | 6/2007 | Gustavsson et al. |
| 2007/0202058 A1 | 8/2007 | Calton |
| 2007/0225727 A1 | 9/2007 | Matsuhisa et al. |
| 2009/0005320 A1 | 1/2009 | Kneller |
| 2009/0208612 A1 | 8/2009 | Reiser et al. |

FOREIGN PATENT DOCUMENTS

| | | |
|---|---|---|
| JP | 58-134963 A | 8/1983 |
| KR | 100 839 794 B1 | 6/2008 |
| WO | 2006/025072 A3 | 3/2006 |

OTHER PUBLICATIONS

All American Pharmaceutical, "Gluta-Zorb," retrieved from, http://glutazorb.com/, retrieved on Dec. 29, 2010, 2 pages.

Bomber Blend Whey Protein Ingredient Label, http://www.davedraper.com/bomberblend-ingredient-label.html., published Jan. 19, 2008, 3 pages.

Bozzo et al., "Antiproliferative effect of conjugated linoleic acid in caco-2 cells: Involvement of PPARγ and APC/β-catenin pathways," Chemico-Biological Interactions 169(2): 110-121, 2007.

Collins English Dictionary—Complete and Unabridged, 12$^{th}$ Edition 2014 © HarperCollins Publishers 1991, 1994, 1998, 2000, 2003, 2006, 2007, 2009, 2011, 2014.

Berardi, "Covering Your Nutritional Acids (and Bases)," T Nation, Internet Article published Jul. 11, 2003, https://www.t-nation.com/diet-fat-loss/covering-your-nutritional-acides-and-bases, 15 pages.

Hatcher et al., "Impact of Genotype and Environment on the Quality of Amber Durum Wheat Alkaline Noodles," Cereal Chemistry 86:4, 2009, 11 pages.

Heffley, "To Your Health; What is the difference between l-glutamine and glutamine, and the same for the other amino acids?", Internet Article published Jun. 23, 2006, 4 pages.

Muttucumaru et al., "Formation of High Levels of Acrylamide during the Processing of Flour Derived from Sulfate-Deprived Wheat," J. Agric. Food Chem., 54, 8951-8955, 2006.

Phillips, "The Health Wonders of the Alkaline Diet," retrieved from http://www.articlesbase.com/health-articles/the-health-wonders-of-the-alkaline-diet-517357.html, 2 pages.

Pritchard, "Is Creatine a Safe Supplement for Teenagers?" Internet article, https://www.livestrong.com/article/517667-is-creatine-a-safe-supplement-for-teenagers/, 2017, 2 pages.

Ruchi et al., "Tribulus terrestris fruit extract protects against oxidative stress-induced apoptosis," Pharmaceutical Biology 45(8): 619-625, Database Biosis [online], retrieved from BIOSIS PAN-PREV200700598057, 2007.

Tisdale, "Inhibition of Lipolysis and Muscle Protein Degradation by EPA in Cancer Cachexia," Nutrition 12(1): S31-S33, 1996.

Wang et al., "Cardiovascular disease prevention of cranberry vinegar," NutritionalSciencesJournal 32(4): 129-132, 2007.

* cited by examiner

ALKALIZED ORGANIC PHARMACEUTICAL OR NUTRACEUTICAL COMPOSITION

BACKGROUND

Technical Field

Description of the Related Art

Many, if not most of the foodstuffs consumed by mammals are acidic in nature. This is particularly true of processed foods such as convenience foods or "junk foods". Many foods are made more acidic during processing to improve their taste and also to facilitate preservation. Most food preservatives are more effective in a low pH environment. In addition any additives and food preservatives are themselves acidic, for example, citric acid, malic acid, ascorbic acid, phosphoric acid, benzoic acid, acetic acid and sulphur dioxide.

Besides ingesting a variety of acidic products, a typical modern diet is composed almost entirely of acid-forming foods, such as animal proteins, grains, legumes, and table salt (sodium chloride). Sixty percent of table salt is a reactive chloride ion which, in solution, has an affinity for hydrogen ions, generating corrosive, carcinogenic hydrochloric acid. Sebastian's team showed that chloride is responsible for salt's ability to induce hypertension, as well as urinary nitrogen and calcium losses, signaling erosion of muscle and bone.

Unbuffered, acids dissolve calcium from bones and teeth, and facilitate soft-tissue calcification. They corrode cartilage and attack arteries, which (in self-defense) secrete a protective, buffering lipid-calcium complex. The body dilutes the acids by retaining water, but this action, combined with arteriosclerosis, creates hypertension, which can lead to heart and cerebrovascular disease.

Acid-producing (high-protein, high-salt) diets have been shown to cause urinary stones. Salt-induced chloride acidosis has been found to cause irritability, hyperactivity and insomnia.

Many organic substances are not stable in an acidic environment and may convert into dangerous by-products. In addition, the ingestion of acidic foods and acid-generating foods may cause the body to slip into metabolic acidosis. Acidosis is a condition in which the body's fluids tend to have a higher acid content than normal. It is a clinical disturbance caused by kidney failure due to decreased pH level characterized by an increase in total body acid. The body has a variety of ways to compensate for mild acidosis, but prolonged acid ingestion can result in weakness, headache, heavy or rapid breathing. Severe acidosis can lead to acidemia, which is a buildup of acids in the blood, resulting in a coma or death.

A team from the department of medicine and the General Clinical Research Center at the University of California, San Francisco, led by Anthony Sebastian, recently published research revealing that typical Western diets produce slight chronic systemic metabolic acidosis in humans. The research shows that such a diet accelerates aging, corrodes muscle and bone, and suppresses growth hormone secretion (Frassetto et al. 2001, Eur J Nutr 40, pp 200-213).

Even mild acidosis can hinder athletic performance along with every day human life. Lactic acid is a metabolic acid that is known to hinder athletic performance. Lactic acid is produced by muscle tissue to obtain energy by metabolizing glucose in the absence of oxygen.

Lactic acid is produced by almost all tissues in the human body and is formed by glycolysis. Glycolysis is a chemical process in which glucose is broken down to pyruvic acid. The pyruvic acid, mixed with oxygen is converted to carbon dioxide, water and ATP. ATP provides energy for muscle contraction. Contracting muscles obtain ATP from glycolysis of glucose stored in the blood stream and in the glycogen that is stored in the muscles.

At first, pyruvic acid and small amounts of ATP are generated. As the muscles continue to contract with exercise, the circulatory system cannot provide a high enough supply of oxygen. In this condition (which may occur in seconds in some individuals), most of the pyruvic acid produced in the breakdown of glucose is converted to lactic acid rather than carbon dioxide, water and ATP.

The human body's response to a normal buildup of lactic acid is to transport it from the cramped muscle via the blood stream to the liver where it is converted back to pyruvic acid, then to carbon dioxide, water and ATP when the oxygen supply is adequate.

As the lactic acid is carried around the blood stream it impairs the body's normal function. Lactic acid is formed in large amounts during strenuous exercise, which leads to muscle cramps, fatigue and failure. Lactic acid fatigue is commonly called "the burn or hitting the wall". This results in muscle fatigue. As more oxygen becomes available, the lactic acid is converted back to pyruvic acid, then into carbon dioxide, water and ATP. But unfortunately by this time, most humans will have quit exercising to allow the body to re-oxygenate.

Therefore, as the body becomes more acidic, strength, endurance and overall athletic performance including weight training, all decrease.

An object of the present invention is to provide compositions that enhance health and wellbeing, and methods of using them.

BRIEF SUMMARY

In one aspect the invention provides a pharmaceutical or nutraceutical composition comprising an alkalized organic substance selected from the group comprising proteins, carbohydrates, lipids, amino acids, vitamins, therapeutic agents and mixtures thereof.

In another aspect the invention provides a method for preparing a pharmaceutical or nutraceutical composition comprising an alkalized organic substance, the method comprising mixing the organic substance with a base such that the pH of the resulting composition is between 7 and 15; wherein the organic substance is selected from the group comprising proteins, carbohydrates, lipids, amino acids, vitamins, therapeutic agents and mixtures thereof.

In another aspect the invention provides a method for treating a disease or condition selected from the group comprising inflammatory diseases, congestive heart failure, ischemic heart disease, heart attack, arrhythmia, cardiomyopathy, high cholesterol and/or triglycerides; MELAS, gyrate atrophy, mitochondrial cytopathies, Parkinson's disease, Huntington's disease, amyotrophic lateral sclerosis, stroke, Alzheimer's disease, myopathies, Duchenne's muscular dystrophies, myophosphorylase deficiency (McArdle's disease), neuromuscular disease, muscular dystrophies, rheumatoid arthritis, osteoporosis, gout, hepatitis, cancer, viral infections and autoimmune disorders, the method comprising administering a therapeutically effective amount of an alkalized organic substance selected from the group comprising proteins, carbohydrates, lipids, amino acids, vitamins, therapeutic agents and mixtures thereof to a subject in need thereof.

In another aspect the invention provides a method for treating or preventing diseases or conditions associated with inflammation comprising administering a therapeutically effective amount of an alkalized organic substance selected from the group comprising proteins, carbohydrates, lipids, amino acids, vitamins, therapeutic agents and mixtures thereof to a subject in need thereof.

In one embodiment the diseases or conditions associated with inflammation are selected from the group comprising asthma, heart disease, gingivitis and autoimmune disorders including lupus.

In another aspect the invention provides a method of increasing physical strength and/or increasing muscle mass in a subject comprising administering an effective amount of an alkalized organic substance selected from the group comprising proteins, carbohydrates, lipids, amino acids, vitamins, therapeutic agents and mixtures thereof to the subject.

In another aspect the invention provides a method of increasing physical endurance and/or physical efficiency in a subject comprising administering an effective amount of an alkalized organic substance selected from the group comprising proteins, carbohydrates, lipids, amino acids, vitamins, therapeutic agents and mixtures thereof to the subject.

In another aspect the invention provides a method of preparing a subject for physical activity and/or speeding up recovery of a subject after physical activity, comprising administering an effective amount of an alkalized organic substance selected from the group comprising proteins, carbohydrates, lipids, amino acids, vitamins, therapeutic agents and mixtures thereof to the subject prior to or following the physical activity.

In the aspects of the invention described above:

In one embodiment the organic substance comprises a lipid, in particular one or more esterified oils, such as particular cetyl myristoleate and/or conjugated linoleic acid.

In one embodiment the organic substance is a carbohydrate, preferably maltodextrin.

In one embodiment the organic substance comprises protein, in particular whey protein concentration and/or grain protein. Preferably, the grain protein is rice or wheat protein.

In one embodiment the organic substance is an amino acid, preferably L-glutamine.

In one embodiment the organic substance comprises a therapeutic agent. Preferably, the therapeutic agent is selected from the group comprising *Tribulus terrestris* extract, Saw Palmetto extract, Sarsaparilla extract, Taxadrol hidafolia or mixtures thereof.

In one embodiment the organic substance comprises calcium malate.

In one embodiment the organic substance comprises at least one of esterified oils, maltodextrin, protein, glutamine and *Tribulus terrestris* extract.

In one embodiment the alkalized composition comprises one or more of disodium phosphate, magnesium glycerol phosphate, magnesium stearate, di-potassium phosphate, soda ash, sodium bicarbonate, sodium phosphate and potassium phosphate.

BRIEF DESCRIPTION OF THE SEVERAL VIEWS OF THE DRAWINGS

The invention will now be described with reference to the drawings in which.

DETAILED DESCRIPTION

Definitions

Figure 1:
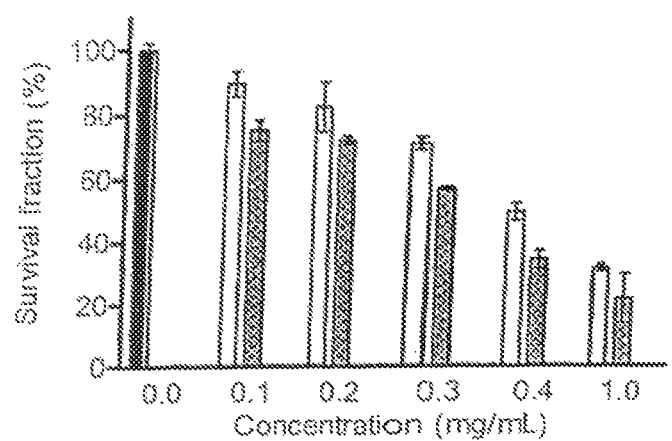
FIG. 1 is a graph showing the antiproliferative effects of non-processed fats (white columns) vs. alkalized oils (grey columns) against the human acute promyelocyte leukemia HL-60 after 72 h continuous exposure, as assessed by the MTT-dye reduction assay. Each data point represents the arithmetic mean±sd of 8 separate experiments.
Figure 2:
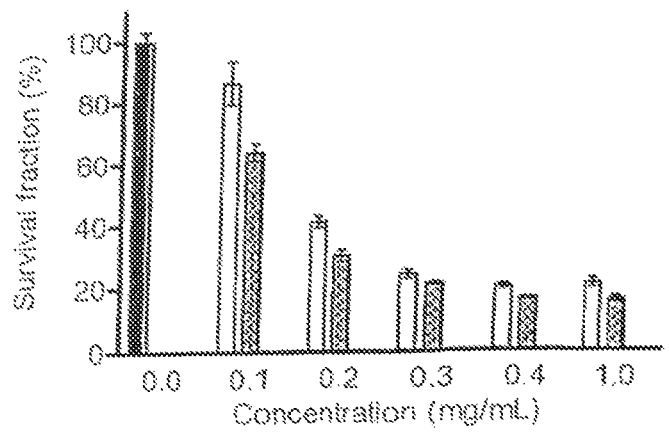
FIG. 2 is a graph showing the effects of non-processed fats (white columns) vs. alkalized oils (grey columns) against the human chronic myeloid leukemia LAMA-84 after 72 h continuous exposure, as assessed by the MTT-dye reduction assay. Each data point represents the arithmetic mean±sd of 8 separate experiments.
Figure 3:
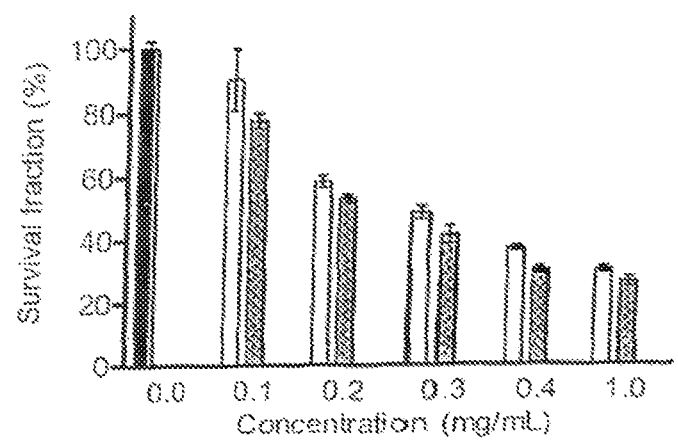
FIG. 3 is a graph showing the effects of non-processed fats (white columns) vs. alkalized oils (grey columns) against the human Hodgkin-lymphoma HD-MY-Z after 72 h continuous exposure, as assessed by the MTT-dye reduction assay. Each data point represents the arithmetic mean±sd of 8 separate experiments.
Figure 4:
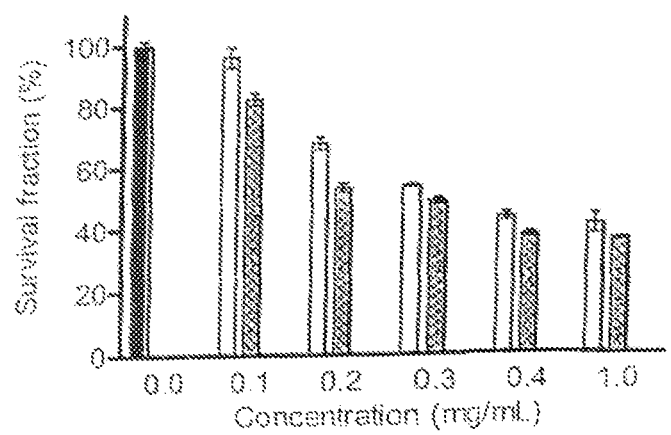
FIG. 4 is a graph showing the antiproliferative effects of non-processed fats (white columns) vs. alkalized oils (grey columns) against the human multiple myeloma OPM-2 after 72 h continuous exposure, as assessed by the MTT-dye reduction assay. Each data point represents the arithmetic mean±sd of 8 separate experiments.
Figure 5:
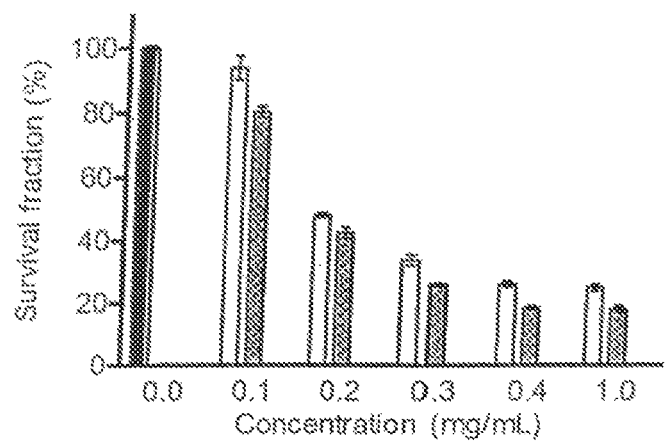
FIG. 5 is a graph showing the antiproliferative effects of non-processed fats (white columns) vs. alkalized oils (grey columns) against the human multiple myeloma U-266 after 72 h continuous exposure, as assessed by the MTT-dye reduction assay. Each data point represents the arithmetic mean±sd of 8 separate experiments.
Figure 6:
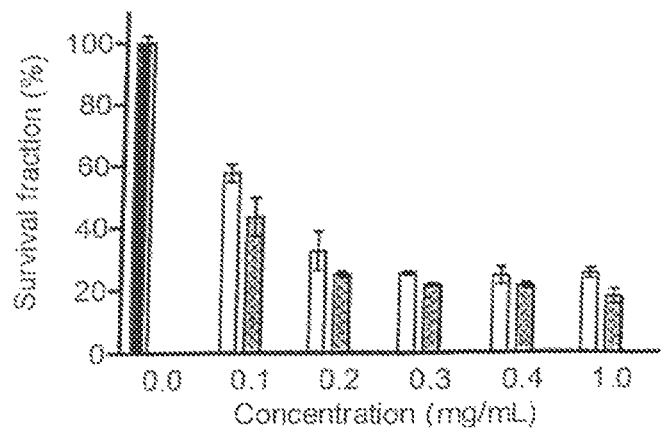
FIG. 6 is a graph showing the antiproliferative effects of non-processed fats (white columns) vs. alkalized oils (grey columns) against the human multiple myeloma RPMI— after 72 h continuous exposure, as assessed by the MTT-dye reduction assay. Each data point represents the arithmetic mean±sd of 8 separate experiments.

As used herein the term "alkalized organic substance" refers to a composition that includes one or more organic substances and sufficient base such that the composition has a pH of between 7 and 15. Preferably, the pH of the composition is in the range 9-15, more preferably 11-15, most preferably 12-14.

The pH of a solid composition is defined as the pH of a 5% solution of the solid composition in deionized water.

As used herein the term "base" refers to a chemical compound that donates hydroxy ions or absorbs hydrogen ions when dissolved in water.

As used herein the term "physical strength" means the ability of exerting force through muscle action.

As used herein the term "physical endurance" means the ability to sustain vigorous muscle activity for at least 90 seconds, preferably at least 4 minutes, sometimes for more than 60 minutes.

The term "therapeutically effective amount" as used herein, means that amount of an active compound, or a material, composition or dosage form comprising an active compound, which is effective for producing some desired therapeutic or prophylactic effect, commensurate with a reasonable benefit/risk ratio.

The term "treatment" as used herein in the context of treating a condition or disease, relates generally to treatment and therapy, whether of human or animal, in which some desired therapeutic effect is achieved, for example, the inhibition of progress of the condition, and includes a reduction in the rate of progress, a halt in the rate of progress, amelioration of the condition, and cure of the condition. Treatment as a prophylactic measure (i.e., prophylaxis) is also included.

"Treatment" also includes combination treatments and therapies, in which two or more treatments or therapies are combined, for example, sequentially or simultaneously. For example, a therapeutically effective amount of a compound of formula (I) could be combined with or used in conjunction with radiation therapy or chemotherapy in the treatment of cancer.

The term "subject" as used herein refers to a human or non-human mammal. Examples of non-human mammals include livestock animals such as sheep, horses, cows, pigs, goats, rabbits, deer, ostriches and emus; and companion animals such as cats, dogs, rodents, and horses. Preferably, the subject is a human.

The term "comprising" as used herein means "consisting at least in part of". When interpreting each statement in this specification that includes the term "comprising", features other than that or those prefaced by the term may also be present. Related terms such as "comprise" and "comprises" are to be interpreted in the same manner.

As used herein the term "increasing physical efficiency" means the increased ability to perform physical activity which is reflected by improvement of $VO_2$ max.

As used herein the term "therapeutic agents" means agents that may be used to improve health or treat or prevent disease. Therapeutic agents include pharmaceuticals, plant or herbal extracts, nutraceuticals and antioxidants.

Alkalized Compositions of the Invention

The pharmaceutical or nutraceutical compositions of the invention comprise an alkalized organic substance. The organic substance is selected from the group comprising proteins, carbohydrates, lipids, amino acids, vitamins, therapeutic agents and mixtures thereof.

In one embodiment the organic substance is a lipid. Mixtures of different types of lipids may be used. In one embodiment the lipid is selected from the group comprising fats, oils, fatty acids, fatty esters, sterols, isoprenoids, phosphatides and cerebrosides.

Preferably, the lipid is an esterified oil or mixture of esterified oils such as cetyl myristoleate and conjugated linoleic acid. Preferably the pharmaceutical or nutraceutical composition consists of the lipid and base and optionally excipients.

In one embodiment the organic substance is a protein, in particular whey protein concentrate and/or grain protein. Preferably, the grain protein is rice or wheat protein.

In another embodiment the organic substance is a carbohydrate. The carbohydrate may be selected from the group comprising sugars, starches, celluloses and gums. Starch, maltodextrin and glucose are preferred carbohydrates for use in the invention.

In one embodiment the organic substance is an amino acid. L-glutamine is a preferred amino acid for use in the invention.

In a further embodiment the organic substance is a vitamin. In one embodiment the vitamin is selected from the group comprising vitamin A, beta-carotene, vitamin B1, vitamin B2, vitamin B3, vitamin B6, folic acid, vitamin B12, vitamin C, vitamin D, vitamin K, niacin, pantothenic acid and biotin.

In yet a further embodiment the organic substance is a therapeutic agent. In one embodiment the therapeutic agent is an antioxidant or a herbal extract. Preferred therapeutic agents include saw palmetto extract, *Tribulus terrestris* extract, Taxadrol hidafolia, Sarsaparilla extract and summa extract.

The alkalized compositions of the invention may be prepared by adding a base to an organic substance such that the pH of the composition is between 7-15. Preferred bases include disodium phosphate, magnesium glycerol phosphate, magnesium stearate, di-potassium phosphate, soda ash, sodium bicarbonate, sodium phosphate and potassium phosphate.

The compositions of the invention are pharmaceutical or nutraceutical compositions. Therefore, they contain compounds, ingredients, materials, compositions, dosage forms and the like, which are within the scope of sound medical judgment, suitable for use in contact with the tissues of the subject in question (e.g., human) without excessive toxicity, irritation, allergic response, or other problems or complications, commensurate with a reasonable benefit/risk ratio. The pharmaceutical or nutraceutical compositions may also comprise carriers, diluents and/or excipients. Each carrier, diluent, excipient, etc., must also be pharmaceutically or nutraceutically "acceptable" in the sense of being compatible with the other ingredients of the formulation.

Suitable pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives. The compositions can also be formulated as pills, capsules, granules, tablets (coated or uncoated), (injectable) solutions, solid solutions, suspensions, dispersions, solid dispersions (e.g., in the form of ampoules, vials, creams, gels, pastes, inhaler powder, foams, tinctures, lipsticks, drops, sprays, or suppositories). The formulation can contain (in addition to the alkalized organic substance) fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art. One skilled in this art may further formulate the compositions of the invention in an appropriate manner, and in accordance with accepted practices, such as those described in *Remington's Pharmaceutical Sciences*, Gennaro, Ed., Mack Publishing Co., Easton, Pa. 1990.

The alkalized compositions may be prepared in the form of a powder, capsule, tablet, liquid, oil, soft gel or other means known in the art. The alkalized compositions can be taken as dietary supplements or can be incorporated into foodstuffs such as beverages, baked goods, etc. The amount of organic substance and type of substance can vary depending on the application and the amount and type of base added. The amount that should be administered to each subject will need to be calculated depending on the formulation, the gender, the age and the activity level of the subject.

Uses of Compositions of the Invention

The pharmaceutical or nutraceutical compositions of the invention buffer the extreme stomach acidity associated with pathological conditions such as gastritis. In addition, by decreasing the acidic load in the body, the compositions of the invention prevent acidosis, thereby enhancing strength, energy, endurance and overall athletic performance.

As can be seen from the Examples, the alkalized organic substances of the invention provide a number of health benefits and may be useful in the treatment and prevention of a wide range of diseases.

The invention consists in the foregoing and also envisages constructions of which the following gives examples only.

EXAMPLES

Example 1

Typical Formulations of Alkalized Compositions

Example 1 provides typical formulations of the alkalized compositions of the invention.

Formulation A

| | |
|---|---|
| maltodextrin | 25 g |
| starch | 25 g |
| di-sodium phosphate | 100 mg |
| di-potassium phosphate | 100 mg |
| magnesium glycerol phosphate | 25 mg |

Formulation B

| | |
|---|---|
| whey protein concentrate | 20 g |
| di-sodium phosphate | 100 mg |
| di-potassium phosphate | 100 mg |
| magnesium glycerol phosphate | 25 mg |
| natural vanilla | 2 mg |
| sucralose | 2 mcg |

Formulation C

| | |
|---|---|
| maltodextrin | 100 g |
| soda ash | 1 mg |
| magnesium glycerol phosphate | 15 mg |
| Kre-Alkalyn creatine | 750 mg |

Formulation D

| | |
|---|---|
| soy bean oil | 5 g |
| calcium malate | 25 mg |
| di-sodium phosphate | 25 mg |
| tenox ™ antioxidant | 25 mg |

Formulation E

| | |
|---|---|
| L-glutamine | 500 mg |
| magnesium stearate | 5 mg |
| soda ash | 2 mg |
| sodium bicarbonate | 3 mg |
| in a gelatine capsule | 100 mg |

Formulation F

| | |
|---|---|
| *Tribulus Terrestris* extract | 150 mg |
| Saw Palmetto extract | 25 mg |
| Potassium phosphate | 10 mg |
| Sodium phosphate | 50 mg |
| Gelatine capsule | 100 mg |

Formulation G

| | |
|---|---|
| Esterified Oils (consisting of cetyl myristoleate and conjugated linoleic acid) | 350 mg |
| di-sodium phosphate | 25 mg |
| Magnesium glycerol phosphate | 25 mg |

Formulation H

| | |
|---|---|
| *Tribulus Terrestris* Extract | 100 mg |
| Sarsaparilla Extract | 50 mg |
| Taxadrol hidafolia | 500 mg |
| Sodium bicarbonate | 10 mg |
| Potassium bicarbonate | 10 mg |

Formulation I

| | |
|---|---|
| Whey Protein Concentrate | 20 grams |
| Grain Protein (Rice, Wheat) | 5 grams |
| di-sodium phosphate | 100 mg |
| di-potassium phosphate | 100 mg |
| Magnesium glycerol phosphate | 25 mg |

Example 2

Endurance and Stamina

Study

Study administering an alkalized maltodextrin (Formulation A)-vs-unalkalized maltodextrin to 12 endurance athletes in the off season phase.

Procedures 6 subjects were administered 25 grams of alkalized maltodextrin 30 minutes before exercise and 6 subjects were administered 25 grams of unalkalized maltodextrin for 2 weeks. No changes were made to diet or off season training.

Endurance and Stamina levels were tested at the beginning of the study and every day for two weeks.

The testing equipment used were Life Fitness computerized bicycles. These systems are able to monitor heartbeat and revolutions per minute.

Results

The pre test showed that the unalkalized maltodextrin group was in a bit better shape than the alkalized maltodextrin group. The alkalized maltodextrin group was barely able to work up to and maintain a level 4, at 100 rpms for 20 minutes, while the unalkalized maltodextrin group could maintain a level 4, at 100 rpms for 20 minutes.

Unmodified Maltodextrin

Not much progress was made during week 1. Measurements were taken three times per week. At the end of the second week, the unalkalized maltodextrin group actually had a harder time maintaining a level 4 at 100 rpms for 20 minutes.

Not much change in endurance was noticed during the two week period. And it was noticed in 5 subjects that their heart rate increased, which is a sign of fatigue.

Alkalized Group

The results were dramatic. At the end of Week 1 and actually the very first work out, this group was able to work up to and maintain a level 6 at 100 rpms for 20 minutes.

Stamina increased from 20 minutes to 40 minutes showing a 100% increase. Endurance increased from level 4 to level 6 along with the stamina increasing by 66%.

Conclusion

Alkalized maltodextrin dramatically increases endurance and stamina in endurance athletes. Subjects administered alkalized maltodextrin showed stamina increases of 100% and endurance increases of 66% while unalkalized maltodextrin seem to hinder endurance and stamina.

Example 3

Muscle Gain

Study

Rat Study with Alkalized Protein (Formulation B)

Procedures

White male albino rats were used for this study. A control group was used along with a test group. Upon arrival to the lab both groups entered Phase I, stabilization. Stabilization started with changing their diet to a more conventional food source. Good protein and carb levels, low fat. Each rat was weighed at the start and every three days for ten weeks. Rats were randomly selected for test group and control group.

Rats were placed in large 10 gallon glass cages that allowed movement and building of nests. Chew items were also put in the cages to help measure night activity.

Alkalized Protein Administration: Based on human studies, 10 grams per 100 kg of body weight was used. This worked out to 100 mcg/gram of rat starting weight. Alkalized protein was administered daily. The control group received protein of an acidic nature.

The Start

The starting weight of both groups varied, due to different levels of maturity.

Activity and energy levels were extremely low. Neither group was very active.

During the stabilization phase, both control rats and test rats slept during the day, with very low night activity.

| Results | | | |
|---|---|---|---|
| Animal | Weight in grams | % Gained | |
| Test 1 | 524.90 | Start Weight | |
| 01/06/5 | 519.79 | −.97 | |
| 01/10/5 | 519.10 | −1.10 | |
| 01/13/5 | 531.40 | 1.24 | |
| 01/17/5 | 536.00 | 2.11 | |
| 01/20/5 | 538.10 | 2.51 | |
| 01/24/5 | 540.80 | 3.02 | |
| 01/27/5 | 540.80 | 3.02 | |
| 01/31/5 | 543.50 | 3.54 | |
| 02/03/5 | 542.90 | 3.42 | |
| 02/07/5 | 539.10 | 2.70 | |
| 02/10/5 | 536.50 | 2.20 | |
| 02/14/5 | 541.30 | 3.12 | |
| 02/17/5 | 542.80 | 3.41 | |
| 02/21/5 | 557.80 | 6.26 | |
| 02/24/5 | 555.30 | 5.79 | |
| 02/28/5 | 568.30 | 8.26 | |
| 03/05/5 | 562.80 | 7.22 | |
| 03/09/5 | 576.30 | 9.79 | |
| 03/14/5 | 573.80 | 9.31 | |
| 03/17/5 | 568.30 | 8.26 | |
| 03/21/5 | 571.80 | 8.93 | |
| 03/24/5 | 572.30 | 9.03 | Total |
| Test 2 | 327.80 | Start Weight | |
| 01/06/5 | 336.80 | | |
| 01/10/5 | 341.80 | | |
| 01/13/5 | 363.30 | | |
| 01/17/5 | 373.30 | | |
| 01/20/5 | 389.30 | | |
| 01/24/5 | 413.50 | | |
| 01/27/5 | 410.10 | | |
| 01/31/5 | 422.50 | | |
| 02/03/5 | 407.30 | | |
| 02/07/5 | 427.80 | | |
| 02/10/5 | 440.80 | | |
| 02/14/5 | 447.30 | | |
| 02/17/5 | 455.30 | | |
| 02/21/5 | 476.30 | | |
| 02/24/5 | 476.30 | | |
| 02/28/5 | 487.30 | | |
| 03/05/5 | 492.80 | | |
| 03/09/5 | 512.80 | | |
| 03/14/5 | 505.80 | | |
| 03/17/5 | 505.30 | | |
| 03/21/5 | 504.80 | | |
| 03/24/5 | 507.30 | 54.72% | Total |
| Test 3 | 306.30 | Start Weight | |
| 01/06/5 | 343.80 | | |
| 01/10/5 | 344.30 | | |
| 01/13/5 | 362.00 | | |
| 01/17/5 | 371.80 | | |
| 01/20/5 | 384.20 | | |
| 01/24/5 | 408.80 | | |
| 01/27/5 | 409.80 | | |
| 01/31/5 | 423.10 | | |
| 02/03/5 | 410.00 | | |
| 02/07/5 | 424.25 | | |
| 02/10/5 | 444.80 | | |
| 02/14/5 | 448.80 | | |
| 02/17/5 | 463.30 | | |
| 02/21/5 | 463.30 | | |
| 02/24/5 | 473.80 | | |
| 02/28/5 | 480.30 | | |
| 03/05/5 | 481.80 | | |
| 03/09/5 | 506.80 | | |
| 03/14/5 | 496.80 | | |
| 03/17/5 | 499.30 | | |
| 03/21/5 | 495.80 | | |
| 03/24/5 | 491.80 | 60.56% | Total |
| Test 4 | 598.80 | Start Weight | |
| 01/06/5 | 601.30 | | |
| 01/10/5 | 600.80 | | |
| 01/13/5 | 610.50 | | |
| 01/17/5 | 610.80 | | |
| 01/20/5 | 611.30 | | |
| 01/24/5 | 616.20 | | |
| 01/27/5 | 618.80 | | |
| 01/31/5 | 619.40 | | |
| 02/03/5 | 619.80 | | |
| 02/07/5 | 621.10 | | |
| 02/10/5 | 624.30 | | |
| 02/14/5 | 633.30 | | |
| 02/17/5 | 637.30 | | |
| 02/21/5 | 637.80 | | |
| 02/24/5 | 637.90 | | |
| 02/28/5 | 648.80 | | |
| 03/05/5 | 658.80 | | |
| 03/09/5 | 659.30 | | |
| 03/14/5 | 664.80 | | |
| 03/17/5 | 665.80 | | |
| 03/21/5 | 669.80 | | |
| 03/24/5 | 670.80 | 12.02% | Total |
| Test 5 | 335.89 | Start Weight | |
| 01/06/5 | 342.80 | | |
| 01/10/5 | 338.80 | | |
| 01/13/5 | 374.30 | | |
| 01/17/5 | 380.20 | | |
| 01/20/5 | 387.80 | | |
| 01/24/5 | 418.80 | | |
| 01/27/5 | 418.80 | | |
| 01/31/5 | 430.20 | | |
| 02/03/5 | 433.30 | | |
| 02/07/5 | 439.20 | | |
| 02/10/5 | 444.30 | | |
| 02/14/5 | 459.30 | | |
| 02/17/5 | 467.30 | | |

-continued

| Results | | |
|---|---|---|
| Animal Weight in grams | % Gained | |
| 02/21/5 475.80 | | |
| 02/24/5 486.30 | | |
| 02/28/5 492.80 | | |
| 03/05/5 494.30 | | |
| 03/09/5 509.30 | | |
| 03/14/5 509.80 | | |
| 03/17/5 509.80 | | |
| 03/21/5 513.00 | | |
| 03/24/5 515.00 | 53.32% | Total |
| Test 6 307.80 | Start Weight | |
| 01/06/5 320.30 | | |
| 01/10/5 323.80 | | |
| 01/13/5 350.00 | | |
| 01/17/5 357.80 | | |
| 01/20/5 370.80 | | |
| 01/24/5 395.80 | | |
| 01/27/5 404.00 | | |
| 01/31/5 410.60 | | |
| 02/03/5 412.20 | | |
| 02/07/5 413.40 | | |
| 02/10/5 429.80 | | |
| 02/14/5 429.80 | | |
| 02/17/5 429.90 | | |
| 02/24/5 434.30 | | |
| 02/28/5 441.80 | | |
| 03/05/5 441.80 | | |
| 03/09/5 470.80 | | |
| 03/14/5 473.80 | | |
| 03/17/5 473.80 | | |
| 03/21/5 473.80 | | |
| 03/24/5 475.00 | 54.32% | Total |

SUMMARY

There were two ages of groups used for the study. Test 1 and 2 rats were over 1.5 years old. These rats only live for two years. Test 2-6 animals were only 3 months old. So in comparison to humans, test rats 1 and 2 were like adults in their 50's or 60's and test rats 3-6 were like young adults in their teens to 20's.
Results
Test rats 1-2 gained an average of 10.52% in lean muscle weight. Test rats 3-6 gained an average of 55.73%.
Conclusion
Feeding rats alkalized protein increased their gain in lean muscle in seniors by 10.52% and young adults by 55.73%. All rats had more energy and their coats looked healthier and whiter with overall moods appearing to be positive.

Example 4 pH, Energy Levels, Endurance Levels, and Physical Wellbeing

Study
Case Study administering an alkalized maltodextrin/creatine capsule (Formulation C) to 4 Healthy active adults.
Purpose of Study
To measure body pH, energy levels, endurance levels, and physical wellbeing in test subjects.
Procedures
Two subjects were administered 1 capsule daily and two subjects were administered two capsules daily for 30 days. Administration was taken first thing in the morning upon awaking.
pH, energy, endurance and physical levels were measured 3 times daily. The first in the morning before administration, the second midday, and the third in the evening. The following chart was used for measurements.

| Scale: 1-5 Number System | | |
|---|---|---|
| Energy | Endurance | Physical |
| 1—Very energetic | 1—Very | 1—Feel Great |
| 2—Fairly | 2—Good | 2—Good |
| 3—So-So | 3—So-So | 3—So-So |
| 4—A bit sluggish | 4—Not so good | 4—Not so good |
| 5—No energy | 5—Bad | 5—Bad | pH was measured by urinalysis.

The subjects were asked to not change their diet or workout schedules. All 4 subjects were male from ages 25-44.

DEFINITION

Energy
1). A: dynamic quality (narrative energy) B: the capacity of acting or being active (intellectual energy) C: a usually positive spiritual force (the energy flowing through all people)
2). Vigorous exertion of power: EFFORT (investing time and energy)
3). A fundamental entity of nature that is transferred between parts of a system in the production of physical change within the system and usually regarded as the capacity for doing work
4). usable power (as heat or electricity); also: the resources for producing such power
Endurance
1). Permanence, duration
2). The ability to withstand hardship or adversity; especially: the ability to sustain a prolonged stressful effort or activity (a marathon runner's endurance)
3). The act or an instance of enduring or suffering
4). Capacity to endure pain or hardship, fortitude, stamina
Physical*
1). A emotional state or action
2). The overall quality of one's awareness and well-being
3). Strength and power

| Results | | |
|---|---|---|
| Subject 1: | Energy | |
| | Before study: 3.00 (So-So) | |
| | During study: 1.17 (Average) | Very Energetic |
| | Endurance | |
| | Before study: 3.00 (So-So) | |
| | During study: 1.56 (Average) | Very |
| | Physical | |
| | Before study: 2.00 (Good) | |
| | During study: 1.33 (Average) | Feel Great |
| Subject 2: | Energy | |
| | Before study: 3.00 (So-So) | |
| | During study: 1.26 (Average) | Very Energetic |
| | Endurance | |
| | Before study: 3.00 (So-So) | |
| | During study: 1.30 (Average) | Very |

-continued

| | | Results | |
|---|---|---|---|
| | Physical | | |
| Subject 3: | Before study: 3.00 (Good) During study: 1.33 (Average) Energy | | Feel Great |
| | Before study: 4.00 (A bit sluggish) During study: 1.64 (Average) Endurance | | Very Energetic |
| | Before study: 4.00 (Not so good) During study: 1.57 (Average) Physical | | Very |
| Subject 4: | Before study: 4.00 (Not so good) During study: 1.76 (Average) Energy | | Feel Great |
| | Before study: 5.00 (No energy) During study: 3.76 (Average) Endurance | | So-So |
| | Before study: 5.00 (Bad) During study: 3.03 (Average) Physical | | So-So |
| | Before study: 4.00 (Not so good) During study: 3.06 (Average) | | So-So |

| | % Increases: | |
|---|---|---|
| Subject 1: | Energy: | 156.4% |
| | Endurance: | 92.3% |
| | Physical: | 50.3% |
| Subject 2: | Energy: | 138.9% |
| | Endurance: | 130.7% |
| | Physical: | 125.5% |
| Subject 3: | Energy: | 143.9% |
| | Endurance: | 154.7% |
| | Physical: | 127.2% |
| Subject 4: | Energy: | 32.9% |
| | Endurance: | 65.1% |
| | Physical: | 30.7% |

| Average for Study % Increases: | |
|---|---|
| Energy: | 118.0% |
| Endurance: | 110.7% |
| Physical: | 83.4% |

Conclusion

An alkalized maltodextrin/creatine capsule increased energy levels by 118%, endurance and stamina by 110.7% and physical well being by 83.4%.

Example 5

Alkalized Oil

Formulation D

By buffering this oil, we were able to extend the use life of this oil from 1 day (prior art, low pH) to 7 days. This saves the food industry six oil changes a day for frying foods.

Example 6

Strength, Stamina and Endurance

Formulation E.

Week 1-4:

Test subject was administered L-Glutamine HCl (pH 6.0) for 30 days.

Training was three days per week, with 3 days of cardio. Dosage was 500 mg per day the first week and 1000 mg per day for week 2-4.

Week 1: No noticeable changes to strength, stamina or endurance

Week 2-4: No noticeable changes to strength, stamina or endurance

Weeks 5-8:

Test subject was taken off the glutamine HCl (pH 6.0) and administered buffered-Glutamine (pH 12.0) for 30 days. Training was three days per week, with 3 days of cardio. Dosage was 500 mg per day for the 5th week and 1000 mg per day for weeks 6-8.

Week 5: Stamina levels increased during the cardio and training sessions

Week 6-8: Stamina levels continued to increase during the cardio and training sessions approximately by 50%

Strength levels increased by 10%

Endurance levels increased by 35%

Conclusion

Alkalized glutamine outperformed unmodified glutamine in the areas of strength, stamina, and endurance.

Example 7

Antiproliferative Effects of Esterified Oil, Non-Stabilized or Alkalized in a Panel of Human Tumor Cell Lines

| | |
|---|---|
| Esterified Oils (Consisting of cetyl myristoleate and conjugated linoleic acid) | 350 mg |
| di-sodium phosphate | 25 mg |
| magnesium glycerol phosphate | 25 mg |

The antiproliferative effects of alkalized oil (Formula G) was investigated in a comparative fashion vs. non-stabilized fats in a panel of tumor cell lines, representative to some important kinds of human cancer. The panel included the acute promyelocyte leukemia HL-60, the chronic myeloid leukemia LAMA-84, the Hodgkin-lymphoma HD-MY-Z and the multiple myeloma-derived cell lines OPM-2, U-266 and RPMI-23366. All cells were obtained from the German Collection of Microorganisms and Cell Cultures (Brounschweig, Germany) and were routinely maintained under standard conditions RPMI-1640 medium, supplemented with 10% fetal calf serum and L-glutamine, in a 5% $CO_2$ humidified atmosphere (at 37° C.).

For the cytotoxicity assessment exponentially growing cells were plated in 96-well flat-bottomed microplates and after 24 h were treated with the tested fats. The tested compounds were dissolved in DMSO and serially diluted in RPMI-1640 to the desired level. For each concentration at least 8 wells were used. After 72 h exposure the cellular viability was monitored by the standard MTT-dye reduction assay, as described elsewhere [1], with minor modification [2].

The tested fats, both conventional and processed, exerted strong inhibition of the proliferation of malignant cells, in a concentration-dependent manner. This allowed the calculation of the corresponding $IC_{50}$ values, i.e., concentration causing half-maximal inhibition of cell viability, as merit of the antiproliferative potency of tested compounds.

The acute promyelocyte leukemia HL-60 demonstrated significant sensitivity to both conventional and stabilized fats, although the latter proved to be significantly more active as evident by the point-to point comparison of survival fractions for every concentration. At the highest level evaluated (1 mg/ml) the conventional fats lowered the fraction of living cells to 31.7%, while the alkalized oils decreased the percentage of viable cells to 21.9%. The $IC_{50}$ values were 0.41 mg/ml for the conventional fats vs. 0.32 mg/ml for the alkalized oils respectively.

Significant antiproliferative effects were established in LAMA-84 cells as well. As in the preceding cell line, the stabilized, alkalized oils proved to be superior antiproliferative agents as evidenced by the MTT-data. At the highest concentration tested the non-processed fats reduced the cellular viability by ca. 79%, while the alkalized oils lowered it by approximately 84%. The $IC_{50}$ values obtained were 0.18 mg/ml for the conventional and 0.12 mg/ml for the alkalized oils.

The evaluation of the antiproliferative effects of tested compounds against the Hodgkin lymphoma derived cell line HD-MY-Z revealed that they exerted strong inhibitory activity, again superior for the alkalized oils. At a concentration of 1 mg/ml the viable cells were 30.7 after exposure to conventional fats and 26.8 after treatment with alkalized oils. The superiority of the alkalized oils in terms of potency is corroborated by the calculated $IC_{50}$ values—0.27 mg/ml for the conventional fats vs. 0.22 mg/ml for the processed ones.

The results for the three multiple myeloma-derived cell lines also demonstrated the superiority of the alkalized oils, vs. the non-stabilized ones.

The presented data indicate that throughout the panel of malignant cells the alkalized oils proved to exert superior antiproliferative effects vs. the non-buffered ones, as evidenced by point-to-point comparison of survival fractions after treatment with equivalent concentrations as well as by juxtaposition of the calculated $IC_{50}$ values. It is well appreciated in the art, that the antiproliferative potency of a given compound in vitro is governed by its stability under the experimental conditions. Thus, considering the equivalent controlled conditions of the experiment, the observed greater activity of alkalized oils could be ascribed solely to the superior stability afforded by the processing manipulations.

REFERENCES

1. Mosmann, T., Rapid colorimetric assay for cellular growth and survival: application to proliferation and cytotoxicity assays. *J Immunol Methods*, 1983. 65(1-2): p. 55-63.
2. Konstantinov, S. M., H. Eibl, and M. R. Berger, BCR-ABL influences the antileukaemic efficacy of alkylphosphocholines. *Br J Haematol*, 1999. 107(2): p. 365-80.

TABLE 1

Antiproliferative effects of non-processed fats vs. alkalized oils in a panel of human tumor cell lines, as assessed by the MTT-dye reduction assay after 72 h continuous exposure.

| Cell line | Origin | $IC_{50}$ (mg/ml) Non-processed fats | $IC_{50}$ (mg/ml) Buffered fats |
|---|---|---|---|
| HL-60 | Acute promyelocyte leukemia | 0.41 ± 0.07 | 0.32 ± 0.03 |
| LAMA-84 | Chronic myeloid leukemia | 0.18 ± 0.04 | 0.12 ± 0.02 |
| HD-MY-Z | Hodgkin lymphoma | 0.27 ± 0.04 | 0.22 ± 0.03 |
| OPM-2 | Multiple myeloma | 0.12 ± 0.02 | 0.08 ± 0.01 |
| U-266 | Multiple myeloma | 0.32 ± 0.05 | 0.24 ± 0.06 |
| RPMI | Multiple myeloma | 0.20 ± 0.03 | 0.17 ± 0.01 |

Example 8

Study Administering an Alkalized *Tribulus Terrestris* Extract Vs. Acidic *Tribulus Terrestris* Extract

| | |
|---|---|
| *Tribulus Terrestris* Extract | 500 mg |
| Sodium bicarbonate | 10 mg |
| Potassium bicarbonate | 10 mg |

Purpose of Study

To see if alkalized *tribulus* herb outperforms acidic *tribulus* herb.

Procedures

Subject for 30 days was administered 500 mg of acidic *tribulus* first thing in the A.M. on an empty stomach, taken as a capsule. Subject was then switched to 500 mg of alkalized *tribulus* taken first thing in the A.M. on an empty stomach. Test subject was an adult male experienced in the sport of bodybuilding.

Strength levels were noted at the beginning of the study based on the following lifts:

Declined chest press

Leg Press

Shoulder Press

Pull downs

The testing equipment was located at the local Oz Fitness Center. Testing was done once per week. No change to diet or exercise program.

Results: Pre-Test

| | |
|---|---|
| Declined chest press | 185 lbs × 10 reps |
| Leg Press | 405 lbs × 10 reps |
| Shoulder Press | 90 lbs × 10 reps |
| Pull downs | 150 lbs × 10 reps |

Week 1 Acidic *Tribulus*:

| | |
|---|---|
| Declined chest press | 185 lbs × 10 reps |
| Leg Press | 405 lbs × 10 reps |
| Shoulder Press | 90 lbs × 10 reps |
| Pull downs | 150 lbs × 10 reps |

Week 2 Acidic *Tribulus*:

| | |
|---|---|
| Declined chest press | 190 lbs × 10 reps |
| Leg Press | 425 lbs × 10 reps |
| Shoulder Press | 95 lbs × 10 reps |
| Pull downs | 160 lbs × 10 reps |

Week 3 Acidic *Tribulus*.

| | |
|---|---|
| Declined chest press | 190 lbs × 10 reps |
| Leg Press | 425 lbs × 10 reps |
| Shoulder Press | 95 lbs × 10 reps |
| Pull downs | 160 lbs × 10 reps |

Week 4 Acidic *Tribulus*:

| | |
|---|---|
| Declined chest press | 195 lbs × 10 reps |
| Leg Press | 435 lbs × 10 reps |
| Shoulder Press | 95 lbs × 10 reps |
| Pull downs | 170 lbs × 10 reps |

Week 1 Alkalized *Tribulus*:

| | |
|---|---|
| Declined chest press | 225 lbs × 10 reps |
| Leg Press | 455 lbs × 10 reps |
| Shoulder Press | 100 lbs × 10 reps |
| Pull downs | 170 lbs × 10 reps |

Week 2 Alkalized *Tribulus*:

| | |
|---|---|
| Declined chest press | 245 lbs × 10 reps |
| Leg Press | 495 lbs × 10 reps |
| Shoulder Press | 105 lbs × 10 reps |
| Pull downs | 190 lbs × 10 reps |

Week 3 Alkalized *Tribulus*:

| | |
|---|---|
| Declined chest press | 275 lbs × 10 reps |
| Leg Press | 585 lbs × 10 reps |
| Shoulder Press | 110 lbs × 10 reps |
| Pull downs | 180 lbs × 10 reps |

Week 4 Alkalized *Tribulus*:

| | |
|---|---|
| Declined chest press | 315 lbs × 10 reps |
| Leg Press | 605 lbs × 10 reps |
| Shoulder Press | 125 lbs × 10 reps |
| Pull downs | 200 lbs × 10 reps |

Conclusion:

The alkalization of *tribulus*-vs-acidic *tribulus* results were overwhelming.

| | Acidic *Tribulus* % Increase | Alkalized *Tribulus* % Increase |
|---|---|---|
| Declined press | 5.4% | 70.27% |
| Leg Press | 7.4% | 19.38% |
| Shoulder Press | 5.5% | 39.88% |
| Pull downs | 13.3 | 33.33% |

On a 4 lift average, the Alkalized *Tribulus* showed an average increase in strength of 32.815% over the 4 lift average of Acidic *Tribulus*.

The above examples illustrate the practice of the invention. It will be appreciated by those skilled in the art that the invention can be carried out with numerous modifications and variations.

While the fundamental novel features of the invention have been shown and described, it should be understood that various substitutions, modifications, and variations may be made by those skilled in the arts, without departing from the spirit or scope of the invention. Accordingly, all such modifications or variations are included in the scope of the invention as defined by the following claims:

The invention claimed is:

1. A pharmaceutical or nutraceutical composition, consisting of an alkalized organic substance, wherein:
   the alkalized organic substance consists of one or more alkalized amino acids;
   one of the one or more alkalized amino acids is alkalized L-glutamine;
   the composition has a pH of between 9 and 15; and
   the composition does not contain creatine.

2. A pharmaceutical or nutraceutical composition, consisting of one or more amino acids, and at least one base added to said organic substance to obtain an alkalized organic substance, wherein:
   the alkalized organic substance consists of one or more alkalized amino acids;
   one of the one or more alkalized amino acids is alkalized L-glutamine:
   the at least one base is one or more of disodium phosphate, magnesium glycerol phosphate, magnesium stearate, di-potassium phosphate, soda ash, sodium bicarbonate, sodium phosphate and potassium phosphate;
   the composition has a pH of between 9 and 15; and
   the composition does not contain creatine.

3. A method for preparing a pharmaceutical or nutraceutical alkalized organic substance composition, the method comprising mixing (i) one or more amino acids, with (ii) sufficient base to obtain a composition having a pH that is between 9 and 15, thereby obtaining an alkalized organic substance composition consisting of one or more alkalized amino acids,
   wherein:
   one of the one or more alkalized amino acids is alkalized L-glutamine; and
   the alkalized organic substance composition does not contain creatine.

4. The method of claim 3, wherein the base comprises one or more of disodium phosphate, magnesium glycerol phosphate, magnesium stearate, di-potassium phosphate, soda ash, sodium bicarbonate, sodium phosphate and potassium phosphate.

5. A method of increasing physical strength and/or muscle mass in a subject, or for increasing physical endurance and/or physical efficiency in a subject, the method comprising administering to the subject an effective amount of the pharmaceutical or nutraceutical composition of claim 1.

6. The method of claim 5, wherein the pH of between 9 and 15 of the pharmaceutical or nutraceutical composition results from mixing one or more amino acids with one or more of disodium phosphate, magnesium glycerol phosphate, magnesium stearate, di-potassium phosphate, soda ash, sodium bicarbonate, sodium phosphate and potassium phosphate, to obtain said one or more alkalized amino acids.

7. A method of increasing physical strength and/or muscle mass in a subject, or for increasing physical endurance and or physical efficiency in a subject, the method comprising administering to the subject an effective amount of the pharmaceutical or nutraceutical composition of claim 2.

8. The composition of claim 2, wherein the base consists of soda ash and at least one of disodium phosphate, magnesium glycerol phosphate, magnesium stearate, di-potassium phosphate, sodium bicarbonate, sodium phosphate and potassium phosphate.

9. The composition of claim 2, wherein the base consists of soda ash, sodium bicarbonate and at least one of disodium phosphate, magnesium glycerol phosphate, magnesium stearate, di-potassium phosphate, sodium phosphate and potassium phosphate.

10. The method of claim 3, wherein the base consists of soda ash and at least one of disodium phosphate, magnesium glycerol phosphate, magnesium stearate, di-potassium phosphate, sodium bicarbonate, sodium phosphate and potassium phosphate.

11. The method of claim 3, wherein the base consists of soda ash, sodium bicarbonate and at least one of disodium phosphate, magnesium glycerol phosphate, magnesium stearate, di-potassium phosphate, sodium phosphate and potassium phosphate.

* * * * *